United States Patent [19]

Guseinov

[11] 4,259,247

[45] Mar. 31, 1981

[54] PROCESS FOR THE PRODUCTION OF ETHYLENE OXIDE

[76] Inventor: Nazim M. Guseinov, ulitsa Gusi-Gadzhieva, 3, kv. 12, Baku, U.S.S.R.

[21] Appl. No.: 781,495

[22] Filed: Mar. 25, 1977

Related U.S. Application Data

[63] Continuation of Ser. No. 607,815, Aug. 25, 1975, abandoned.

[51] Int. Cl.$^3$ ............................................. C07D 301/10
[52] U.S. Cl. ................................................ 260/348.35
[58] Field of Search ..................... 260/348.5 F, 348.35

[56] References Cited

FOREIGN PATENT DOCUMENTS

| 486735 | 9/1952 | Canada ............................ 260/348.5 R |
| 1059428 | 6/1959 | Fed. Rep. of Germany .... 260/348.5 R |
| 2237188 | 2/1973 | Fed. Rep. of Germany .... 260/348.5 F |
| 573575 | 11/1945 | United Kingdom ............. 260/348.5 R |

*Primary Examiner*—Norma S. Milestone
*Attorney, Agent, or Firm*—Haseltine and Lake

[57] ABSTRACT

A process for the production of ethylene oxide, which comprises effecting ethylene oxidation with oxygen in the presence of carbon dioxide, the components being present in a volume ratio of 5-15 ethylene to 10-15 oxygen to 75-85, carbon dioxide. The process is effected at a temperature of from 290° to 300° C. and a pressure of from 35 to 50 atm. The components form an upward flow moving at a speed of from 10 to 12 m/sec. The oxidation is carried out in the presence of a silver catalyst on a carrier likewise forming an upward flow which moves at a speed of from 4 to 6 m/sec. The reaction mixture resulting from the oxidation procedure contains the desired product, the unreacted ethylene and the unreacted oxygen. The desired product is recovered from the mixture.

1 Claim, No Drawings

PROCESS FOR THE PRODUCTION OF ETHYLENE OXIDE

CROSS-RELATED APPLICATION

This application is a continuation of co-pending application 607,815 filed Aug. 25, 1975, now abandoned.

The present invention relates to processes for the production of ethylene oxide.

Ethylene oxide finds wide application in organic synthesis as a valuable feedstock for manufacturing antifreezes, polymeric materials, biologically-and physiologically active agents, various dopants, surface-active substances and the like.

It is known in the art to produce ethylene oxide by direct oxidation of ethylene with air in the presence of a silver catalyst on a carrier. See British Pat. No. 1,379,797.

Said prior art process comprises mixing ethylene with air heated to a temperature of 300° C. The mixing proceeds until the concentration of ethylene in the resultant ethylene-air mixture reaches 3.15 to 3.30 percent by volume, a level ensuring that the mixture becomes explosion proof. Further, the ethylene-air mixture is admixed with a silver catalyst on a carrier and sent in an upward flow for oxidation, the ethylene-air mixture moving at a speed of from 10 to 12 m/sec while the catalyst moves at a speed of from 4 to 6 m/sec. The oxidation reaction is effected at a temperature of from 290° to 300° C. The reaction mixture produced in said reaction contains ethylene oxide, the unreacted ethylene, the unreacted oxygen, carbon dioxide, nitrogen and water. Then said reaction mixture and the catalyst are delivered into a separator to be separated therein, whereupon the desired product is recovered from the mixture, the excess of nitrogen and the carbon dioxide formed in the process being continuously withdrawn from the system. The water forming in the process is likewise completely withdrawn from the system.

The unreacted ethylene may be subjected to secondary oxidation. To this end, the unreacted ethylene recovered from the reaction mixture is again admixed with air heated to a temperature of 300° C., until the level of ethylene in the ethylene-air mixture reaches 2 to 3.5 percent by volume. Said mixture is sent for secondary oxidation of the unreacted ethylene in a counterflow with respect to the descending catalyst which may be that of the primary oxidation step, the ethylene-air mixture rising at a speed of 5 m/sec. The secondary oxidation of the unreacted ethylene is effected at a temperature between 260° and 280° C.

The use of air in the prior art process leads to the accumulation of an inert gas, viz. nitrogen, in the reaction system whose excess is to be withdrawn from the system, requiring a special process in which losses of ethylene and ethylene oxide are an inevitable liability. Furthermore, as the amount of nitrogen increases, the ethylene oxidation rate slows down and the ethylene oxide level in the reaction products diminishes to an unacceptable 1.3 to 1.45 percent by volume. To make matters still worse, the accumulation of nitrogen reduces the catalyst to an undesirably low 350 to 400 kg/cu.m. Yet another disadvantage of said known process consists in its low feed (air and ethylene) capacity associated with the low limits of ethylene concentration in the air-gas mixture. Still another disadvantage of said prior art process consists in that, under the specified process conditions, the ethylene oxidation involves the use of a catalyst exhibiting poor activity (containing no adsorbed oxygen on the surface thereof) so that the ethylene oxidation rate undergoes variation and the reaction space is thus utilized incompletely. Since the reaction is an exothermic one, the inefficient utilization of the reaction space disrupts the isothermy of the process which in turn causes a further reduction in the reaction rate and desired product concentration.

It is an object of the present invention to provide a process for the production of ethylene oxide conducive to a higher concentration of the desired product in the reaction products as well as to a higher feed capacity and an improvement in catalyst performance.

In accordance with the foregoing object as well as other objects, the present invention resides in that there is proposed a process for the production of ethylene oxide by ethylene oxidation with oxygen, the ethylene and the oxygen froming an unpward flow moving at a speed of from 10 to 12 m/sec, in the presence of a silver catalyst on a carrier likewise forming an upward flow which moves at a speed of from 4 to 6 m/sec, at a temperature of from 290° to 300° C. to produce a reaction mixture containing the desired product, the unreacted ethylene and the unreacted oxygen, the desired product being subsequently recovered from said reaction mixture. In accordance with the invention, the oxidation of ethylene with oxygen is effected in the presence of carbon dioxide at a volume ratio of the components of 5-15 ethylene to 10-15 oxygen to 75-85 carbon dioxide and at a pressure of from 35 to 50 atm.

Under the foregoing conditions of the process, an insignificant amount of carbon dioxide and water is formed alongside ethylene oxide. The starting carbon dioxide serves as the diluent. The oxygen-carbon dioxide system has a favorable effect on the ethylene oxidation process because the ratio of the starting components may be varied over a wide range, providing for a high selectivity of the process and for a high rate of the ethylene oxidation reaction.

At the selected temperatures, the above-mentioned speeds of the upward flow made up of ethylene, oxygen and carbon dioxide provide for a stable upwash whatever the height of the reactor. Said speeds of the catalyst provide for the necessary time of contact of the upwash with the catalyst.

The catalyst may be e.g. a silver catalyst on a carrier modified with Cl, Cd, Ca and Se simultaneously. Said dopants combine to improve the selectivity and thermal stability of the catalyst.

In order that the concentration of the desired product may be raised, it is recommended that the unreacted ethylene and the unreacted oxygen be recovered from said reaction mixture and the unreacted ethylene be subjected to oxidation with the unreacted oxygen with the aid of a silver catalyst on a carrier in the presence of carbon dioxide at a volume ratio of the components of 7.0-7.4 unreacted ethylene to 12.5-12.9 unreacted oxygen to 79.7-80.5 carbon dioxide at a temperature of from 260° to 280° C. and a pressure of from 35 to 50 atm, said components forming an upward flow which moves in a counter flow at a speed of 5 m/sec with respect to said catalyst.

Under the foregoing conditions, the unreacted ethylene is oxidized, raising the concentration of the ethylene oxide product.

In order to improve the activity of the catalyst, prior to the process the silver catalyst on a carrier is preferably saturated with oxygen by passing oxygen through said catalyst, the amount of oxygen being from 1 to 5 percent by volume of the overall feed quantity (ethylene, oxygen and carbon dioxide).

Any amount of oxygen within said limits is enough for an adsorbed layer of oxygen required to enable an ethylene oxidation reaction to be formed on the catalyst surface. For this reason the catalyst never loses its activity and the reaction space is completely utilized.

Carbon dioxide with its higher specific heat as against nitrogen provides for intensive and uniform cooling in the course of ethylene oxidation, so that the oxidation procedure may be effected under isothermic conditions.

With carbon dioxide rather than nitrogen used as the diluent, there are no losses of the initial ethylene and the ethylene oxide product while withdrawing from the system the carbon dioxide formed in the reaction, since its amount is very small.

Furthermore, as the proposed process dispenses with nitrogen, there is no need for special energy-intensive equipment which would otherwise be required to recover nitrogen from the reaction mixture.

The aforementioned volume ratio of ethylene, oxygen and carbon dioxide, which varies over a fairly wide range, makes for an ideal mixing of the components and boosts the mass transfer between the gaseous and solid phases. Hence a rise in the ethylene oxidation rate, which raises the concentration of ethylene oxide in the reaction products by 1.5 times, improves the performance of the catalyst by 1.5 to 2 times and raises the feed capacity of the process by 80 percent as against the prior art process utilizing air as the oxidizing agent. The selectivity of the proposed process is 3 to 3.5 volume percent higher that that of the known process.

The process of this invention is realized as follows.

Carbon dioxide is admixed with oxygen. The resultant mixture is heated to a temperature of from 200° to 250° C. and delivered to the mixing arrangement of the reactor whereinto ethylene and the catalyst are supplied in an independent flow. The volume ratio of the reaction components is selected within the following limits: 5-15 ethylene; 10-15 oxygen and 75-85 carbon dioxide. Said components and the catalyst are sent for oxidation in an upward flow: the speed of the flow made up of ethylene, oxygen and carbon dioxide is from 10 to 12 m/sec; the speed of the catalyst flow is from 4 to 6 m/sec.

The ethylene oxidation reaction is effected at a temperature of from 290° to 300° C. and a pressure of from 35 to 50 atm. The reaction results in a reaction mixture containing ethylene oxide, carbon dioxide (the starting carbon dioxide plus that which is formed in the reaction) as well as the unreacted ethylene and the unreacted oxygen. The reaction mixture together with the catalyst is supplied into a separator to separate the catalyst. The catalyst having been separated, the reaction mixture is subjected to absorption with glycols, ethylene oxide being the absorbed component. Then the ethylene oxide is recovered from the absorbent by means of rectification. The insignificant amount of carbon dioxide formed in the reaction is recovered from the residue by exposing same to a hot aqueous solution of potash, the water formed in the reaction being likewise recovered by settling. The carbon dioxide thus recovered may be used for preparing the starting stock.

The unreacted ethylene may be subjected to secondary oxidation to raise the concentration of the desired product. To this end, the reaction mixture containing the unreacted ethylene and the unreacted oxygen is contacted with the silver catalyst on a carrier in the presence of carbon dioxide, the components being in a volume ratio of 7.0-7.4 unreacted ethylene to 12.5-12.9 unreacted oxygen to 79.7-80.5 carbon dioxide. The carbon dioxide component may be either fresh gas or that recovered from the reaction mixture formed in the oxidation of ethylene. The oxidation of the unreacted ethylene is effected at a temperature of from 260° to 280° C. and a pressure of from 35 to 50 atm, the reaction components moving in a counterflow at a speed of 5 m/sec with respect to the sinking catalyst. At this secondary oxidation step, use may be made of the catalyst recycled from the oxidation of the starting ethylene.

The reaction mixture containing ethylene oxide produced in the secondary oxidation reaction is separated from the catalyst and the desired product is recovered therefrom. If economic considerations so dictate, carbon dioxide may be recovered from said reaction mixture and utilized for preparing the feed.

In order to raise the activity of the catalyst, prior to the process of ethylene oxidation oxygen may be passed through the catalyst, the quantity of the oxygen ranging from 1 to 5 percent by volume of the total feed.

The invention will be further understood from the following exemplary embodiments thereof.

EXAMPLE 1

Carbon dioxide is admixed with oxygen. The resultant mixture is heated to a temperature of 230° C. and delivered to the mixing arrangement of the reactor where into ethylene and the catalyst are supplied in an independent flow, the reaction components being in a volume ratio of 5 ethylene to 10 oxygen to 85 carbon dioxide. Said components together with the catalyst are sent for oxidation in a upward flow, the flow containing ethylene, oxygen and carbon dioxide moving at 11 m/sec while the catalyst at 5 m/sec. The ethylene oxidation reaction is effected at a temperature of 290° C. and a pressure of 50 atm. The reaction yields a reaction mixture containing 1.45 percent ethylene oxide by volume, 86.35 percent carbon dioxide by volume, 1.35 percent water by volume, 2.88 percent unreacted ethylene by volume and 7.97 percent unreacted oxygen by volume. Said reaction mixture is supplied into a separator to separate the catalyst. After the catalyst has been separated, the reaction mixture is withdrawn from the system and exposed to glycols, the glycols absorbing the ethylene oxide. Then the absorbent is subjected to rectification with a view to recovering the ethylene oxide. In the course of rectification, the water is removed from the system and the carbon dioxide formed in the oxidation reaction is recovered with the aid of a hot solution of potash.

The overall conversion level of ethylene amounts to 42.5 percent by volume. The yield of ethylene oxide on the basis of converted ethylene is 68.2 percent by volume.

EXAMPLE 2

In this example, the procedure of ethylene oxidation to ethylene oxide duplicates that of Example 1 except that the process conditions are different: the components are in a volume ratio of 10 ethylene to 15 oxygen to 75 carbon dioxide; the component flow moves at a speed of 10 m/sec; the catalyst flow moves at a speed of 4 m/sec; the ethylene oxidation reaction proceeds at a temperature of 300° C. and a pressure of 35 atm.

The ethylene oxidation reaction produces a reaction mixture of the following composition; vol.%:
ethylene oxide, 2.15
carbon dioxide, 77.06
water, 2.06
unreacted ethylene, 6.82
unreacted oxygen, 11.91.

The overall conversion level is 31.8 percent by volume. The yield of ethylene oxide on the basis of converted ethylene is 67.7 percent by volume.

EXAMPLE 3

In this example, the procedure of ethylene oxidation to ethylene oxide duplicates that of Example 1 except that the process conditions and the type of catalyst are different: the silver catalyst is modified with Cl, Cd, Ca and Se simultaneously; the componants are in a volume ratio of 15 ethylene to 10 oxygen to 75 carbon dioxide; the feed mixture is preheated to a temperature of 250° C.; the reaction components move in a flow at a speed of 12 m/sec, while the catalyst moves at 6 m/sec; the ethylene oxidation reaction is effected at a temperature of 300° C. and a pressure of 45 atm.

The ethylene oxidation reaction produces a reaction mixture of the following composition, vol.%:
ethylene oxide, 2.2
carbon dioxide, 77.04
water, 2.04
unreacted ethylene, 11.78
unreacted oxygen, 6.94.

The overall ethylene conversion level is 32.2 percent by volume. The yield of ethylene oxide on the basis of converted ethylene is 68 percent by volume.

EXAMPLE 4

In this example, the procedure of ethylene oxidation to ethylene oxide duplicates that of Example 2 except that, after ethylene oxide, water and the newly formed carbon dioxide have been recovered from the reaction mixture, the unreacted ethylene and the unreacted oxygen are involved in secondary oxidation in the presence of carbon dioxide, the components of the secondary oxidation step being in a volume ratio of 7.27 unreacted ethylene to 12.73 unreacted oxygen to 80.0 carbon dioxide.

The secondary oxidation is effected at a temperature of 280° C. and a pressure of 35 atm by contacting said components with a silver catalyst on a carrier, the mixture of said components moving in a counterflow at 5 m/sec with respect to the descending catalyst layer.

The secondary oxidation of the unreacted ethylene produces a reaction mixture of the following composition, vol.%:
ethylene oxide, 1.25
carbon dioxide, 81.2
water, 1.2
unreacted ethylene, 5.42
unreacted oxygen, 10.93.

The overall conversion level of the unreacted ethylene is 25.4 percent by volume. The yield of ethylene oxide on the basis of converted un-reacted ethylene is 67.7 percent by volume.

The two steps of oxidation of the starting and unreacted ethylene produce a reaction mixture of the following composition, vol.%:
ethylene oxide, 3.4
carbon dioxide, 78.26
water, 3.26
unreacted ethylene, 4.93
unreacted oxygen, 10.15.

The overall ethylene conversion level is 50.7 percent by volume. The yield of ethylene oxide on the basis of converted ethylene is 67.5 percent by volume.

EXAMPLE 5

In this example, the ethylene oxidation procedure duplicates that of Example 4 except that the ethylene oxidation reaction proceeds at a temperature of 290° C. and a pressure of 50 atm.

The ethylene oxidation reaction produces a reaction mixture of the following composition, vol.%:
ethylene oxide, 2.05
carbon dioxide, 76.90
water, 1.90
unreacted ethylene, 7.00
unreacted oxygen, 12.15.

The overall ethylene conversion level is 30 percent by volume. The yield of ethylene oxide on the basis of converted ethylene is 68.5 percent by volume. The components of the secondary oxidation reaction are in a volume ratio of 7.4 percent unreacted ethylene to 12.9 unreacted oxygen to 79.7 carbon dioxide. The secondary oxidation of the unreacted ethylene produces a reaction mixture of the following composition, vol.%:
ethylene oxide, 1.05
carbon dioxide, 80.66
water, 0.96
unreacted ethylene, 5.87
unreacted oxygen, 11.46.

The overall conversion level of the unreacted ethylene is 20.6 percent by volume. The yield of ethylene oxide on the basis of converted unreacted ethylene is 68.5 percent by volume.

The two steps of oxidation of the starting and unreacted ethylene produce a reaction mixture of the following composition, vol.%:
ethylene oxide, 3.10
carbon, dioxide, 78.02
water, 3.02
unreacted ethylene, 5.29
unreacted oxygen, 10.47.

The overall ethylene conversion level is 48.1 percent by volume. The yield of ethylene oxide on the basis of converted ethylene is 67.7 percent by volume.

EXAMPLE 6

In this example, the procedures of ethylene oxidation and unreacted ethylene after-oxidation duplicate those of Example 4 except that, prior to the ethylene oxidation step, the silver catalyst is saturated with oxygen at the rate of 1 percent by volume of the overall feed.

The primary oxidation step gives a reaction mixture of the following composition, vol.%:
ethylene oxide, 2.35
carbon dioxide, 77.20
water, 2.20
unreacted ethylene, 6.55
unreacted oxygen, 11.70

The overall ethylene conversion level is 34.5 percent by volume. The yield of ethylene oxide on the basis of converted ethylene is 68.0 percent by volume.

The secondary oxidation components are in a volume ratio of 7.0 unreacted ethylene to 12.5 unreacted oxygen to 80.5 carbon dioxide. The secondary oxidation step uses the recycled silver catalyst from the ethylene oxidation step.

The secondary oxidation of the unreacted ethylene gives a reaction mixture of the following composition, vol.%:
  ethylene oxide, 1.2
  carbon dioxide, 81.6
  water, 1.1
  unreacted ethylene, 5.15
  unreacted oxygen, 10.85.

The overall conversion level of the unreacted ethylene is 25 percent by volume. The yield of ethylene oxide on the basis of converted unreacted ethylene is 68.7 percent by volume.

The two steps of oxidation of the starting and unreacted ethylene produce a reaction mixture of the following composition, vol.%:
  ethylene oxide, 3.55
  carbon dioxide, 78.30
  water, 3.3
  unreacted ethylene, 4.8
  unreacted oxygen, 10.05.

The overall ethylene conversion level is 52.0 percent by volume. The yield of ethylene oxide on the basis of converted ethylene is 68.3 percent by volume.

EXAMPLE 7

In this example, the procedures of ethylene oxidation and unreacted ethylene after-oxidation duplicate those of Example 5 except that, prior to ethylene oxidation, the silver catalyst is saturated with oxygen at the rate of 5 percent by volume of the overall feed. The oxidation of the starting ethylene produces a reaction mixture of the following composition, vol.%:
  ethylene oxide, 2.2
  carbon dioxide, 77.0
  water, 2.00
  unreacted ethylene, 6.8
  unreacted oxygen, 12.0.

The overall ethylene conversion level is 32.0 percent by volume. The yield of ethylene oxide on the basis of converted ethylene is 86.7 percent by volume.

The secondary oxidation components are in a volume ratio of 7.25 unreacted ethylene to 12.75 unreacted oxygen to 80 carbon dioxide. The secondary oxidation reaction uses the silver catalyst recycled from the ethylene oxidation step.

The secondary oxidation of the unreacted ethylene gives a reaction mixture of the following composition, vol.%:
  ethylene oxide, 1.0
  carbon dioxide, 80.9
  water, 0.9
  unreacted ethylene, 5.8
  unreacted oxygen, 11.4.

The overall conversion level of the unreacted ethylene is 20.3 percent by volume. The yield of ethylene oxide on the basis of converted unreacted ethylene is 69.0 percent by volume.

The two steps of oxidation of the starting and unreacted ethylene produce a reaction mixture of the following composition, vol.%:
  ethylene oxide, 3.2
  carbon dioxide, 77.9
  water, 8.9
  unreacted ethylene, 5.35
  unreacted oxygen, 10.65.

The overall conversion of ethylene is 46.5 percent by volume. The yield of ethylene oxide on the basis of converted ethylene is 68.7 percent by volume.

What we claimed is:

1. A process for the production of ethylene oxide, which comprises subjecting ethylene to oxidation with oxygen in the presence of carbon dioxide, said components which are in a volume ratio of 5–15 ethylene to 10–15 oxygen to 75–85 carbon dioxide forming an upward flow moving at a speed of from 10 to 12 m/sec, in the presence of a silver catalyst on a carrier likewise forming an upward flow moving at a speed of from 4 to 6 m/sec, the reaction proceeding at a temperature of from 290° to 300° C. and a pressure of from 35 to 50 atm to yield a reaction mixture containing the desired product, the unreacted ethylene and the unreacted oxygen; and recovering the desired product from said mixture, wherein said catalyst on the carrier, prior to said oxidation, is saturated with oxygen by passing oxygen through said catalyst, the quantity of said oxygen accounting for from 1 to 5 percent by volume of the overall amount of the mixture of the starting components.

* * * * *